(12) United States Patent
Renard et al.

(10) Patent No.: US 8,325,328 B2
(45) Date of Patent: Dec. 4, 2012

(54) SINGLE-PARTICLE LIDAR ANEMOMETRY METHOD AND SYSTEM

(75) Inventors: Alain Renard, Chabeuil (FR); Xavier Lacondemine, Valence (FR); Jean-Pierre Schlotterbeck, Rochefort-Samson (FR)

(73) Assignee: Thales, Neuilly-sur-Seine (FR)

( * ) Notice: Subject to any disclaimer, the term of this patent is extended or adjusted under 35 U.S.C. 154(b) by 140 days.

(21) Appl. No.: 12/842,872

(22) Filed: Jul. 23, 2010

(65) Prior Publication Data
US 2011/0181863 A1 Jul. 28, 2011

(30) Foreign Application Priority Data

Jul. 24, 2009 (FR) ...................................... 09 03660

(51) Int. Cl.
G01P 3/36 (2006.01)
(52) U.S. Cl. ........................................ 356/28; 356/28.5
(58) Field of Classification Search ........ 356/3.01–3.15, 356/4.01–4.1, 5.01–5.15, 6–22, 28, 28.5
See application file for complete search history.

(56) References Cited

U.S. PATENT DOCUMENTS

2003/0217737 A1* 11/2003 Ismailov ....................... 123/494
2004/0027570 A1* 2/2004 Caldwell et al. .............. 356/338

FOREIGN PATENT DOCUMENTS

| EP | 1 749 219 B1 | 10/2008 |
| FR | 2 708 744 A1 | 2/1995 |
| GB | 2 198 840 A1 | 6/1988 |
| WO | 00/16069 A1 | 3/2000 |

* cited by examiner

Primary Examiner — Luke Ratcliffe
(74) Attorney, Agent, or Firm — Baker & Hostetler LLP

(57) ABSTRACT

The present invention concerns a single-particle LIDAR anemometry method and system comprising the continuous emission of one or more light beams through a gas containing particles, said beam being focused onto a measurement volume, a step of detecting a signal backscattered by particles passing through said volume, the method being characterized in that it comprises at least the following phases:
 determining in a time period $\Delta t$ the frequency of each of the pulses included in the backscattered signal;
 distinguishing pulses based on duration and/or intensity and/or frequency-modulation criteria; and
 estimating the displacement velocity of said beam relative to the gas from several of the frequencies determined over the time period $\Delta t$ excluding those corresponding to the pulses distinguished during the preceding step A notable application of the invention is for the measurement of the airspeed of an aircraft.

13 Claims, 7 Drawing Sheets

SINGLE-PARTICLE LIDAR ANEMOMETRY METHOD AND SYSTEM

CROSS-REFERENCE TO RELATED APPLICATIONS

Figure 1:
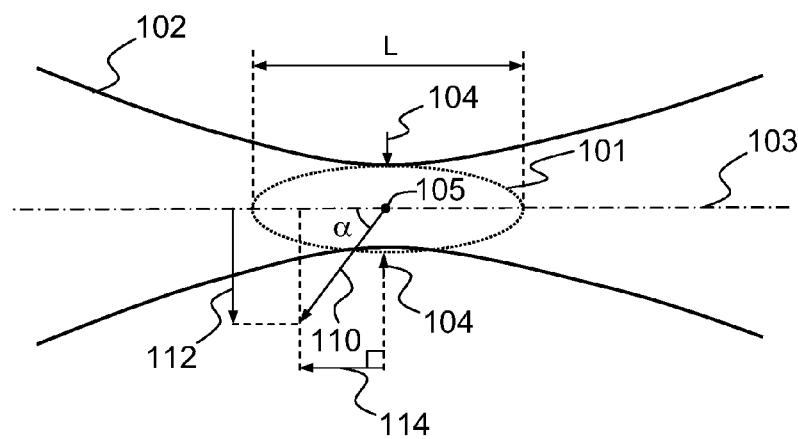

This application claims priority to foreign France patent application No. 0903660, filed on Jul. 24, 2009, the disclosure of which is hereby incorporated by reference in its entirety.

FIELD OF THE INVENTION

The present invention concerns a single-particle LIDAR anemometry method and system. Its application notably is to the measurement of the airspeed of an aircraft.

BACKGROUND OF THE INVENTION

Laser anemometry notably allows the determination of the displacement velocity of a gas, for example a flow of air around an aircraft, by exploiting the presence of suspended aerosols. These aerosols, also termed particles or tracers are for example dust particles or droplets. An optical beam is emitted by a laser and backscattered by aerosols suspended in the air, then the measurement of the frequency shift between an optical reference signal and the backscattered signal allows the velocity of the carrier relative to the aerosols, and thus also to the air, to be determined. The frequency shift thus measured is called the Doppler frequency; it is directly proportional to the component, along the optical propagation axis, of the relative velocity vector of the aircraft with respect to the mass of air. Conventionally, this technology may be split into two classes: multi-particle laser anemometry and single-particle laser anemometry.

Multi-particle laser anemometry consists in probing a relatively large volume of gas—containing a large number of particles (for example several million particles)—at a somewhat large distance from the laser source—of the order of 100 meters, for example—so as to obtain a continuous low-power backscattered signal. This technology requires a high emission power. It therefore requires the use of significant hardware resources and may constitute a safety risk for personnel due to the presence of a high-energy laser.

Single-particle laser anemometry is obtained with the continual emission of a laser over a short distance and focused onto a small volume of gas, thus enabling the observation of particles separately and with a high illumination level (so that the signal-to-noise ratio of the backscattered signal is positive, preferably at least equal to several dB). The backscattered signal then takes the form of a series of pulses that appear randomly, the pulses being produced each time a particle passes through the volume illuminated by the laser. In reality, when the airspeed of an aircraft is measured by laser anemometry, it is not the velocity of the gas that is measured but the velocity of the aircraft relative to this gas (the air in this case), the particles suspended in the air being virtually stationary. It is therefore the displacement of the measurement volume (due to the velocity of the aircraft) which creates a series of pulses. The expression "gas displacement velocity" should be understood to mean "relative velocity" with respect to the light beam.

The single-particle velocity measurement method requires little power and is easily applied to a homogenous medium, in other words to a gas containing particles of similar sizes. However, when it is wished to use this method to measure the gas displacement velocity of a heterogeneous medium, for example to determine the airspeed of an aircraft, the velocity measurements obtained are sometimes inconsistent, notably because of the presence of large particles (pollen grains, ice micro-crystals, rain, etc.) which do not move at the same velocity as the flow of air in which they are suspended, in particular because of the disturbance caused by the aircraft on the nearby mass of air. Since the gas displacement velocity is estimated, for example, by calculating the average velocity of many particles, taking account of particle velocities not moving at the same velocity as the gas lowers said estimation.

Furthermore, the choice of the focal volume, which is to say the volume in which the passage of a particle of the expected size produces a backscattered pulse of sufficiently high amplitude to be useful, is directly related to the distance between the laser source and the focal point of this laser. The choice of said volume—and therefore of the focal distance—results from a compromise between the desire to have sufficient particles to observe and the desire to observe these particles separately from one another. Applied to anemometry on an aircraft, this compromise generally results in a choice of focal distance of the order of several meters, thus being in the zone aerodynamically disturbed by the aircraft. The aerodynamically disturbed flow close to the fuselage leads to the presence of a velocity gradient along the optical propagation axis of the laser. In other words the particles suspended in the air are not moving at the same velocity depending on their position on this optical propagation axis. Thus, a high selectivity along said axis is desirable in order to limit the effect of the velocity gradient.

SUMMARY OF THE INVENTION

The invention improves the precision of the measurement of the displacement velocity of an aircraft relative to the air by single-particle LIDAR. To this end, the subject of the invention is a single-particle anemometry method comprising the continuous emission of a light beam through a gas containing particles, said beam being focused onto a measurement volume, a step of detecting a signal backscattered by particles passing through said volume, said signal comprising a pulse for each particle passage across the field of the beam, the method comprising at least the following phases:

determining in a time period $\Delta t$ the frequency of each of the pulses included in the backscattered signal;
  distinguishing the pulses based on duration and/or intensity and/or frequency-modulation criteria; and
  estimating the displacement velocity of said beam relative to the gas from several of the frequencies determined over the time period $\Delta t$ excluding those corresponding to the pulses distinguished during the preceding step.

This method allows signals backscattered by particles moving at a velocity substantially different to the velocity of the associated gas to be rejected. It allows, for example, signals due to backscatter from a large particle to be eliminated. This is because such signals may be distinguished from others using intensity, duration or frequency-modulation criteria.

Advantageously, the volume of gas onto which the beam is focused is chosen to contain, statistically, only a single particle at a given instant.

Furthermore, the gas illuminated by the laser beam may be heterogeneous. In other words, it may contain particles of any size and shape, for example ice crystals, raindrops and dust particles.

According to one way of implementing the method according to the invention, the phase of determining the pulse frequency or frequencies included in the backscattered signal comprises a step of filtering said signal with a bank of bandpass filters, the frequency bands of said filters together covering a frequency band comprising the Doppler frequencies corresponding to all possible gas displacement velocities. The frequency filtering applied to the backscattered signal notably permits the identification of the frequency or frequencies corresponding to the pulses and the reduction of noise.

Advantageously, the spectral width of the band-pass filters is chosen depending on the expected duration of the pulses included in the backscattered signal. The duration of a pulse of a signal backscattered by the passage of a particle through an oblique beam is a function of the longitudinal position of the particle's passage, which is to say the position at which it passes through the optical axis. Large particles passing outside the focal volume produce a long pulse, which differentiates them from the pulses produced by particles passing through the focal volume of the beam.

The method according to the invention may comprise, at the output of at least one of the band-pass filters, a step of correlating the signal produced by said output with a reference signal, the duration of which is inversely proportional to the principal frequency of said filter and the waveform of which is that of the emitted light signal. The correlation with a reference signal of expected waveform notably allows the elimination of signals produced by particles passing through zones at a distance from the beam waist, which allows good longitudinal selectivity to be obtained, in other words good pulse selectivity along the axis of the light beam.

According to another way of implementing the method according to the invention, each output signal of the band-pass filters is assigned a pulse-presence probability value, said value being a function of the power of the signal at said output.

According to another way of implementing the method according to the invention a Fourier transform is applied to the backscattered signal, said transform being applied to a time-moving window, each frequency spectrum produced by an application of said transform being divided into frequency sub-zones for detecting a pulse in one of said sub-zones, the width of said sub-zones increasing as the frequency decreases.

According to another way of implementing the method according to the invention the pulse distinction phase detects linearly frequency-modulated pulses by generating a time-frequency image of the frequencies associated with the pulses detected in the backscattered signal as a function of time, then executing a shape recognition algorithm to identify in the said image the oblique segments corresponding to the linearly frequency-modulated pulses.

According to another way of implementing the method according to the invention the frequencies corresponding to backscattered pulses, the duration of which is greater than a threshold value, are filtered out during the pulse distinction phase so as to be excluded during the gas displacement velocity estimation phase. The duration threshold value is, for example, optimized as a function of the geometry of the flight axes and characteristics. Filtering the long duration pulses improves the selectivity along the measurement axis and permits the frequencies associated with pulses backscattered from large particles passing through the light beam far from the focal volume of said beam to be ignored.

According to another way of implementing the method according to the invention the frequencies corresponding to the backscattered pulses, the intensity of which is greater than a threshold value, are filtered out during the pulse distinction phase so as to be excluded during the gas displacement velocity estimation phase. This filtering of high intensity pulses notably allows the frequencies of pulses backscattered by large particles passing through the focal volume of the light beam to be ignored. The intensity threshold may be determined in the following manner. Firstly, the size, and by deduction the backscattering cross section, beyond which the particle velocity risks being lowered, is evaluated. Then the threshold is calculated taking into account the power of the optical source and the link budget.

According to another way of implementing the method according to the invention the gas displacement velocity estimation is carried out by determining a Doppler frequency shift $F_D$ equal to the average of the frequencies considered during said estimation, and then by calculating the Doppler velocity corresponding to the frequency $F_D$.

Another subject of the invention is a single-particle anemometry system comprising a light source, preferably a laser, a series of units for detecting signals backscattered by particles illuminated by said beam, the system comprising a signal processing module implementing the anemometry method as described above.

The single-particle anemometry system may be carried by an aircraft in order to measure its airspeed, the emitted light beam being advantageously directed at an angle of illumination of between 30° and 70° to the velocity vector of the aircraft. To determine a three-dimensional velocity vector, a 3D-coordinate system may be chosen with all the axes positioned according to the same velocity-axis angle. Beyond the three non-coplanar axes there is redundancy, and therefore the possibility of performing measurement integrity tests.

The light beam may be focused close to the fuselage of the aircraft, at a distance of between 10 cm and several meters therefrom. This distance is chosen to be far beyond the "boundary layer" so as to have a good bijection between observables and estimated parameters but is also chosen to be as close as possible, so as to reduce power/sensitivity requirements.

Figure 2A:
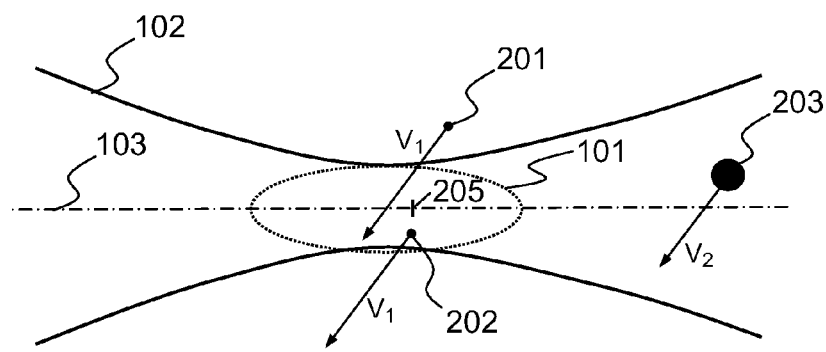
Figure 2B:
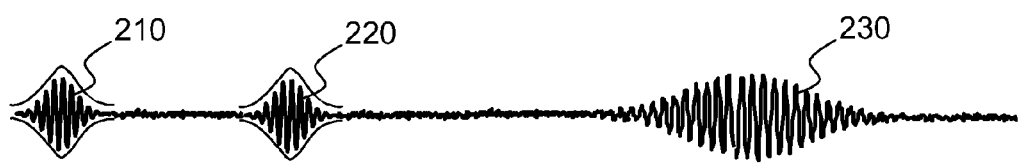
Figure 3A:
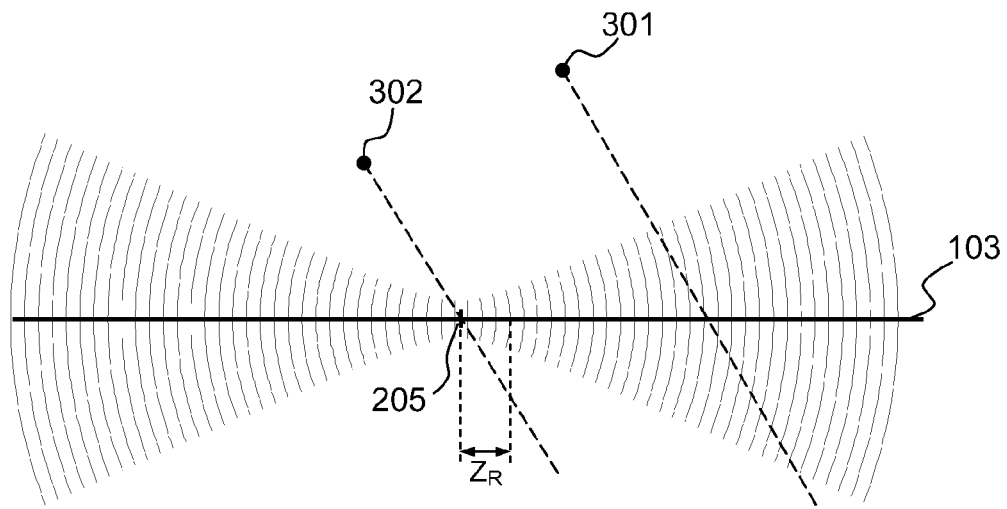
Figure 3B:
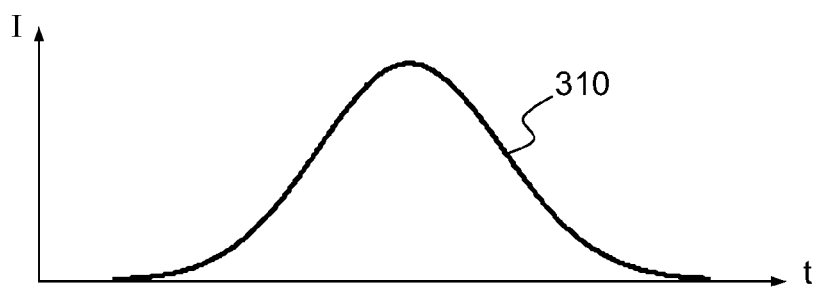
Figure 3C:
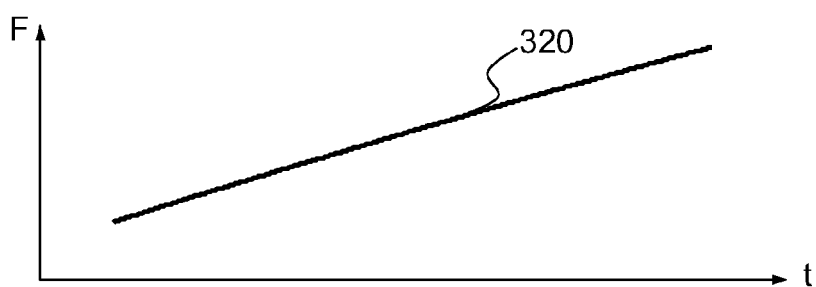
Figure 3D:
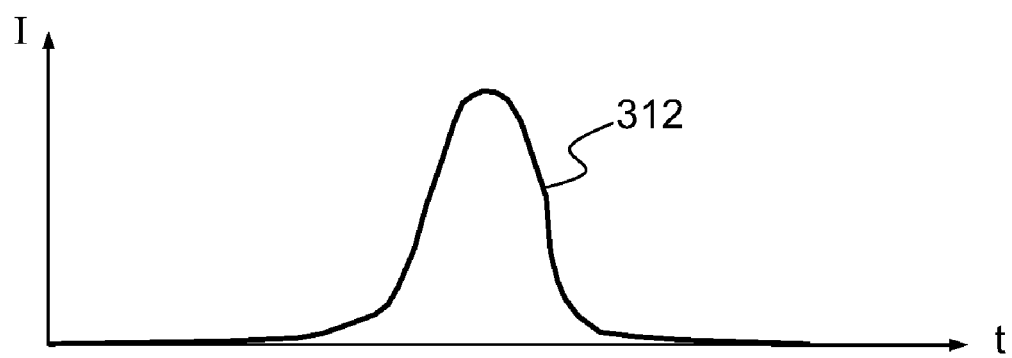
Figure 3E:
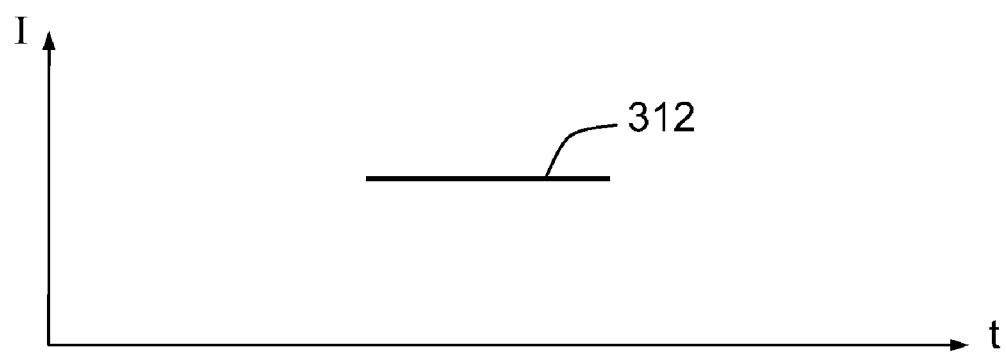
Figure 4:
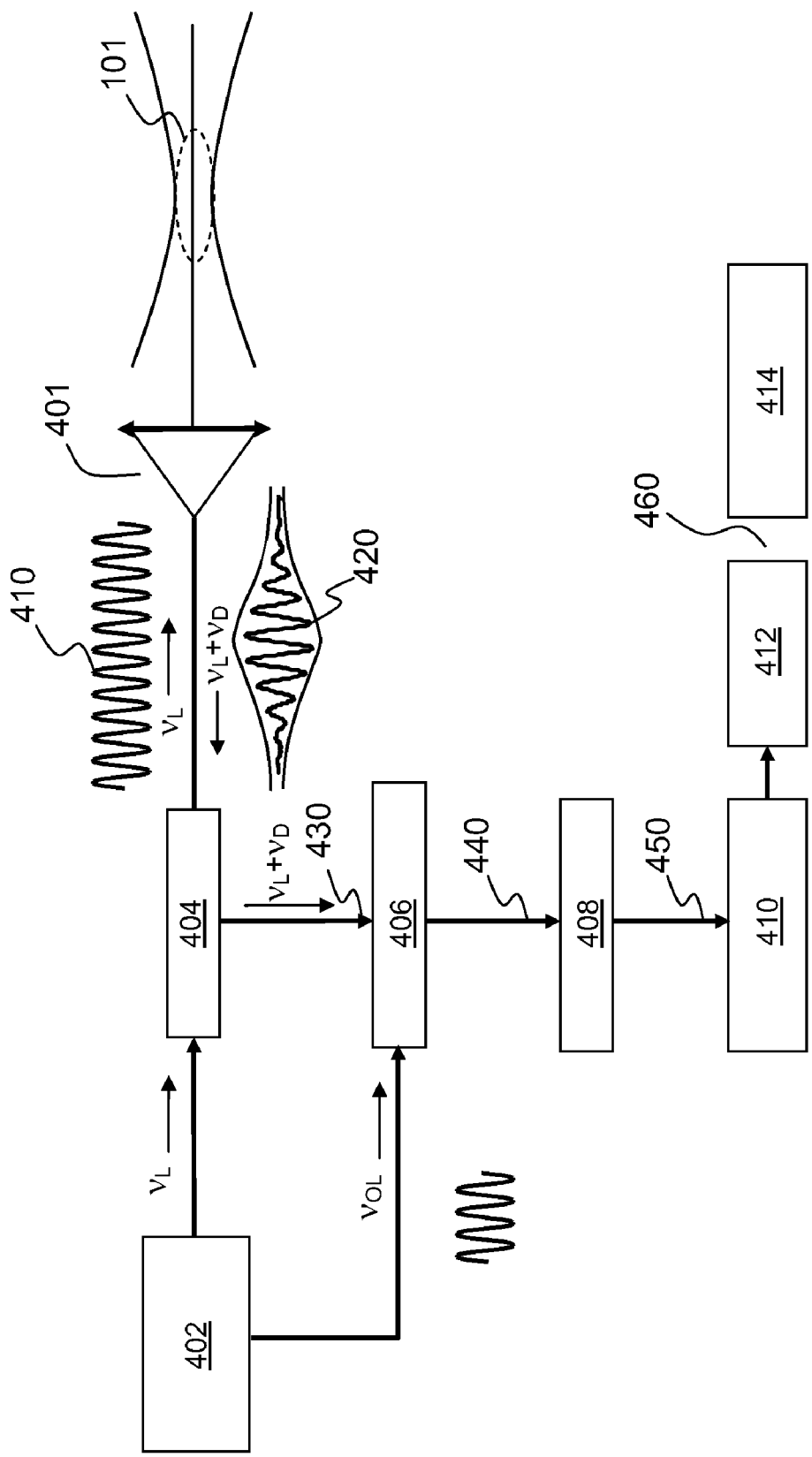
Figure 5:
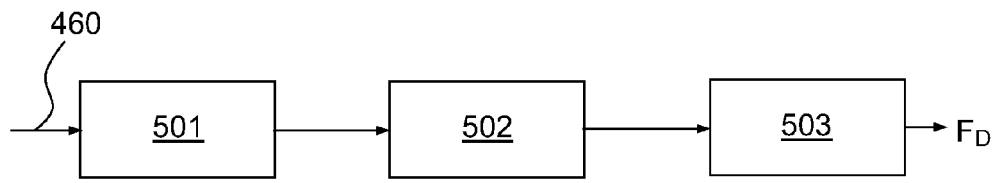
Figure 6A:
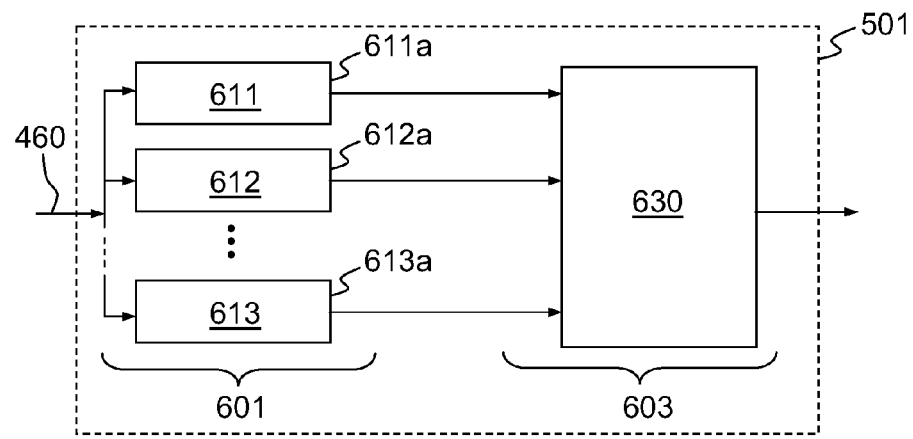
Figure 6B:
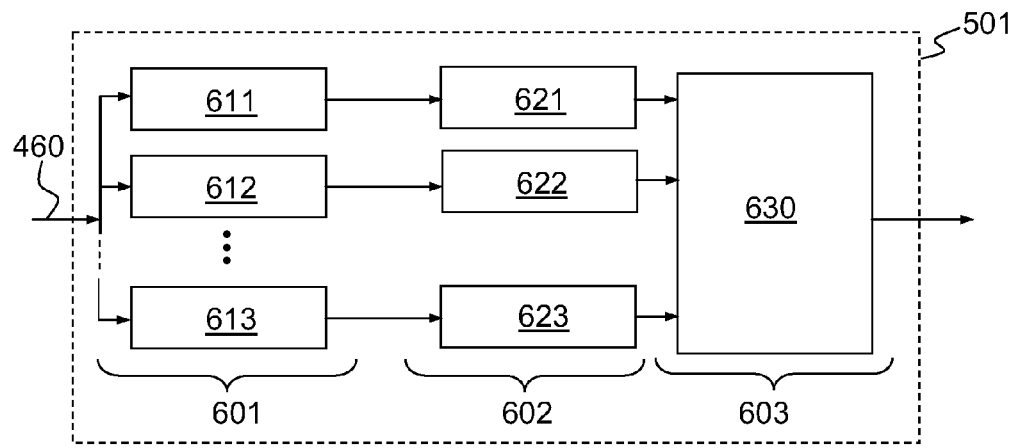
Figure 7:
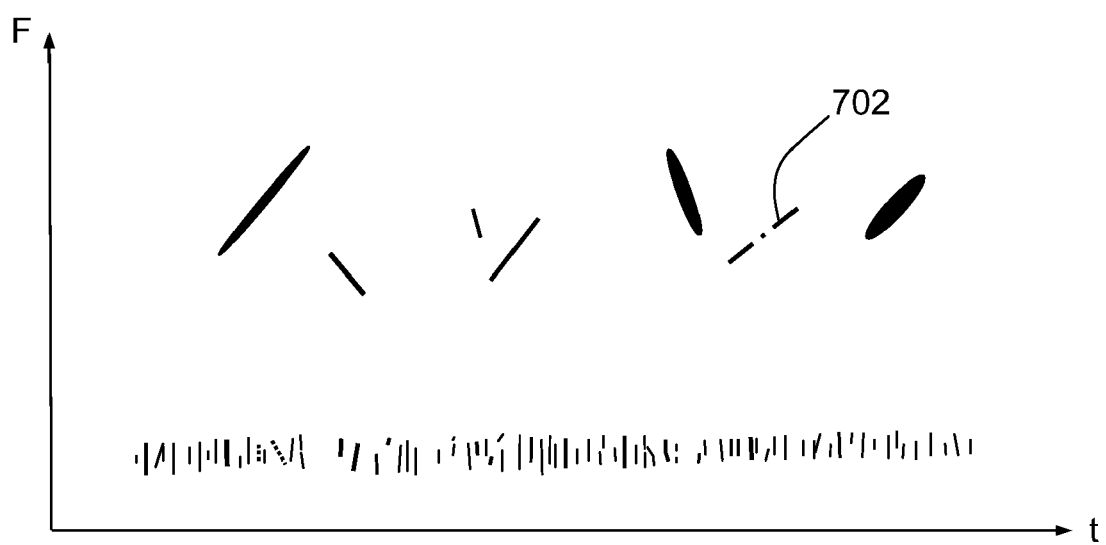
Figure 8:
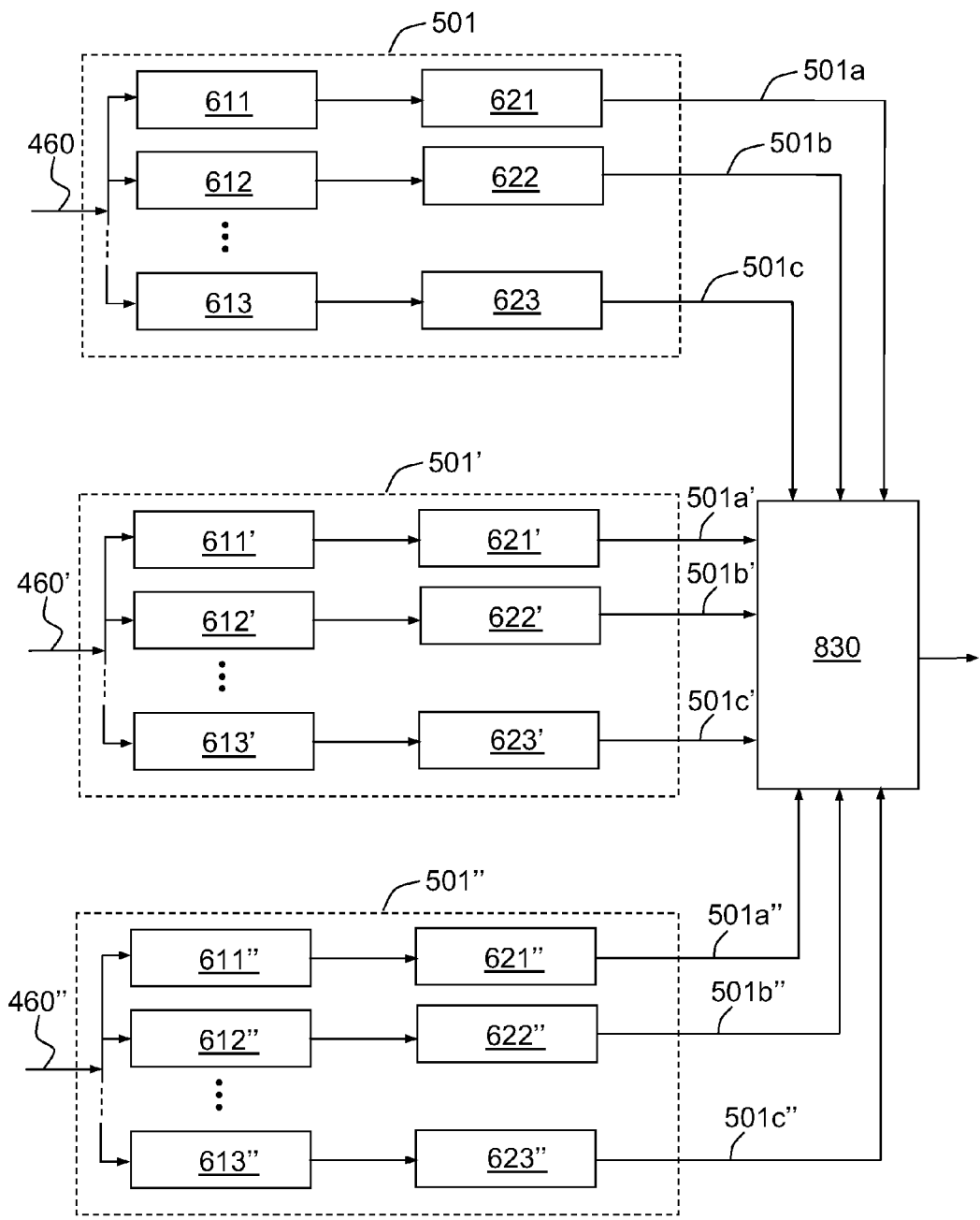

Other features will become clear on reading the following detailed description, given merely by way of non-limiting example and with regard to the appended drawings which show:

FIG. 1, an illustration of a longitudinal cross section of a LIDAR light beam;

FIG. 2a, several particles passing through the optical beam of a LIDAR;

FIG. 2b, signals backscattered by the passage of the particles of FIG. 2a through the field illuminated by the optical beam;

FIG. 3a, the illustration of an example of a configuration in which the pulse backscattered by a first particle is linearly modulated as a function of time and the pulse backscattered by a second particle has a constant frequency during its passage;

FIG. 3b, the curve of intensity as a function of time for the pulse backscattered by the first particle of FIG. 3a;

FIG. 3c, the curve of frequency as a function of time for the pulse backscattered by the first particle of FIG. 3a;

FIG. 3d, the curve of intensity as a function of time for the pulse backscattered by the second particle of FIG. 3a;

FIG. 3e, the curve of frequency as a function of time for the pulse backscattered by the second particle of FIG. 3a;

FIG. 4, a block diagram showing an example of an single-particle anemometry system architecture according to the invention;

FIG. 5, a block diagram showing the processing steps executed by a method according to the invention;

FIG. 6a, a block diagram showing the processing steps executed by a first exemplary method according to the invention;

FIG. 6b, a second exemplary implementation of the first phase of the method according to the invention;

FIG. 7, a time-frequency graph showing the pulse frequencies received in time; and FIG. 8, a block diagram showing the steps of a second exemplary method according to the invention.

DETAILED DESCRIPTION

With regard to clarity, the same references in the various figures denote the same elements.

FIG. 1 shows a longitudinal cross section of a LIDAR light beam. In the example, particles of which it is desired to measure the velocity are spheroids having an average diameter of the order of 0.1 μm. These particles have the advantage of moving at substantially the same speed as the gas in which they are suspended, due to their small size.

The beam envelope 102 is shown in the figure. The focal volume 101 of the beam extends from one side of the beam waist 104 to the other. By way of example, the waist is approximately 50 μm wide and the width L of the beam focal volume 101 along the optical axis 103 is less than 5 mm (Rayleigh zone), which corresponds to a volume 101. The optical axis 103 is directed, for example, so as to make an angle α of 60° with the displacement direction of the particles of which it is desired to measure the velocity. Thus, the velocity vector 110 of a particle 105 can be projected onto at least one transverse axis and one longitudinal axis so as to split this vector 110 into a transverse velocity vector 112 and a longitudinal velocity vector 114. The transverse velocity vector 112 gives an indication of the time it took the particle to pass through the focal volume 101, whereas the longitudinal velocity vector 114 corresponds to the Doppler velocity allowing a precise estimation of the displacement velocity of the particle. According to other ways of implementing the anemometry method, the velocity vector 110 of the particle may be projected onto other axes. It is desired to not obtain particles moving perpendicularly to the optical axis because the longitudinal component of the velocity vector will be zero. Similarly, it is desired to not obtain particles moving parallel to the optical axis because, in this case, the backscattered pulse duration would be mainly dependent on the size of the particle. This is because, the larger the particle, the further away from the beam waist 104 it may be detected.

On an aircraft, the optical beam is for example directed within a range of angles α of between 30° and 70° to the velocity vector of the aircraft, so as to obtain vector components large enough along each axis to avoid the risk of a zero, and thus ambiguous, component.

Large particles, for example with a radius of the order of several microns or tens of microns, backscatter more energy than small particles; they are therefore sometimes detected far from the waist 104, for example 50 cm from the waist 104. Consequently, even if large particles are statistically quite rare in the measurement gas, the detection of these particles is not negligible because of their enlarged field of detection. Now, when it is notably desired to measure the airspeed of an aircraft, these particles do generally not move at the same velocity as the flow of air in which they are carried. In fact, because of aerodynamic disturbance generated near the fuselage, the velocity of large particles is generally not stable; these particles therefore backscatter an undesirable signal, unrepresentative of the actual velocity of the flow of air at the focal point of the optical beam.

FIG. 2a illustrates the passage of several particles through the optical beam of a LIDAR. A first particle 201 and a second particle 202 of substantially equal dimensions pass through the focal volume 101 of the optical beam at a velocity V1, whereas a third particle 203 larger than the two first particles 201 and 202 passes through the field illuminated by the beam outside of the focal volume 101 at a velocity V2 different from V1. The three particles 201, 202, 203 of the example are substantially spherical.

FIG. 2b shows the signals backscattered by the passage of the particles of FIG. 2a through the field illuminated by the beam. A first pulse 210 is produced by the passage of the first particle 201. This first pulse 210 has the waveform of the signal emitted by the LIDAR, i.e., in the example, a Gaussian waveform. A second pulse 220 is next produced by the passage of the second particle 202. This second pulse 220 is substantially of the same waveform as the first 210 and temporally separate from the first pulse 210 because the two particles 201, 202 do not pass through the focal volume 101 at the same time. A third pulse 230 is produced by the passage of the third particle 203, which passes through the beam at some distance from the waist 104 where the beam width is much larger than in the focal volume 101. Consequently, the third particle 203 stays for a longer time in the field illuminated by the light beam, which produces a third pulse 230 longer than the two first pulses 210, 220.

Furthermore, in certain configurations, the pulses backscattered by the particles are frequency-modulated. This modulation occurs when a detected particle passes through the beam non-centrically, in other words, when it does not pass through the central focal point 205.

This situation is illustrated by FIG. 3a, which shows an example of a configuration in which the pulse backscattered by a first particle 301 is linearly modulated as a function of time and the pulse backscattered by a second particle 302 has a frequency constant over its passage. The wavefronts of the light beam converge towards the focal point 205 then diverge as they move away from this point 205. In other words, at the Rayleigh distance $Z_R$, the radius of curvature of the wavefronts is large and, as they move away from this point 205, their radius of curvature decreases.

In the example, the first particle 301 passes through the beam non-centrically. This first particle intersects the wavefronts with a frequency that increases as the particle moves away from the central focal point 205. The particle intersects the planar wavefronts far beyond the Rayleigh distance $Z_R$, which causes a regular frequency variation of the pulse backscattered by the particle. This frequency variation, caused by the curvature of the light beam wavefronts far from the waist, would correspond, for parallel wavefronts, to an unlikely acceleration of the particle of 100 g to 1000 g, which shows that the particle 301 has indeed not passed through the beam through the waist.

FIG. 3b shows the curve of intensity 310 as a function of time for the pulse backscattered by the first particle 301 of FIG. 3a, and FIG. 3c shows the curve of frequency 320 as a function of time for this same pulse. A linear increase in the frequency as a function of time is observed. This phenomenon of frequency deviation is more significant if the focal point is close to the light beam source, which is the case for single-particle anemometry.

To improve the estimation of the velocity of a flow of gas, it is desirable to ignore pulses backscattered by particles that are too large, for the reasons mentioned above.

If such a particle were to pass through the light beam through the focal volume 101, the backscattered pulse may be ignored on the basis of its intensity. This is because the intensity of a pulse backscattered from a particle of significant size, located in the focal volume 101 is clearly higher than the intensity of a pulse backscattered by a particle of the expected size located in the same volume 101.

If a large particle passes through the light beam outside of the focal volume 101, it produces a backscattered pulse with a longer duration than if it had passed through the beam in said volume 101. Furthermore, as the trajectory of this particle is eccentric with respect to the focal point 205, the backscattered pulse is almost linearly frequency-modulated, as illustrated in FIGS. 3a and 3c. It should be noted that a particle of the expected size passing through the light beam outside the focal volume 101 does not produce a backscattered pulse of sufficient amplitude to be detected with satisfactory reliability. Consequently the pulses backscattered by particles of the expected size are due to trajectories that pass close to the focal centre 205; they are therefore not or are only slightly frequency-modulated.

The method according to the invention may use at least one of the abovementioned criteria—amplitude, backscattered pulse duration, frequency modulation—to remove undesired pulses. For example, the method utilises an intensity criterion to perform the filtering when the particle passes through the light beam through the focal volume 101 and a criterion combining frequency modulation and pulse duration to perform the filtering of pulses due to particles passing through the beam outside the focal volume 101.

In the case of an onboard aircraft airspeed measurement, the undesirable pulses are, for example, those resulting from backscatter off ice micro-crystals, raindrops or large dust particles. Furthermore, when the aircraft is close to the ground, when taking off or landing for example, the light beam may be backscattered by the ground, this backscattering being detected in the aircraft in the form of a signal continuous in time.

FIG. 3d shows the intensity curve 312 as a function of time for the pulse backscattered by the second particle 302 of FIG. 3a, and FIG. 3e the frequency curve 322 as a function of time for this same pulse.

It is observed in FIG. 3e that the frequency of the backscattered pulse is constant over the time of passage of the second particle 302 through the field of the light beam.

FIG. 4 shows, via a block diagram, an exemplary single-particle anemometry system architecture. The system comprises a light source, for example a laser 402, a beam splitter 404, an interferometer 406, a detector 408, an amplification and filtering module 410, a digitization module 412 and a digital signal processing block 414.

The laser 402 emits a light beam, in other words an optical signal 410 of frequency $v_L$, to the polarizing beam splitter 404, which receives in return a signal 430 possibly carrying one or more pulses 420 due to the backscatter of the optical signal 410 by one or more particles. If a pulse 420 is received, the pulse is normally affected by a Doppler frequency shift $v_D$ proportional to the longitudinal velocity of said particle(s). The signal 430 containing this pulse 420 is transmitted to the interferometer 406, which interferometer couples said signal 430 with an optical signal of frequency $v_{OL}$, to produce, as output, an optical signal 440 comprising a pulse at the Doppler frequency. This optical signal 440 is transmitted to the detector 408. The detector 408, which is for example a diode, transforms the optical signal 440 output by the interferometer into a high-frequency electrical signal 450. This high-frequency signal 450, which contains for example a pulse transposed to the Doppler frequency, is then amplified, filtered 410 and then digitized 412. The method according to the invention is applicable, more particularly, to the signal output by a digitization module 412. In the example, it may thus be implemented by the digital signal 460 processing block 414.

FIG. 5, shows, via a block diagram, the processing steps executed by a method according to the invention. During a first phase 501, in a short time interval $\Delta t1$ (equal for example to the average expected duration of a pulse), the frequency or frequencies of the pulses carried by the digital signal 460 are determined. The first phase 501 is repeated cyclically, and the frequency or frequencies obtained for each of these cycles is/are stored for a time $\Delta t$.

During a second phase 502, filtering of undesirable signals is performed based on the frequencies stored during a time window $\Delta t2$ shorter than or of the same duration as $\Delta t$, this window $\Delta t2$ containing for example tens or hundreds of time intervals $\Delta t1$. Notably, the pulses linearly frequency-modulated and the backscatter from the ground, in the case of onboard aircraft anemometry, are rejected. As explained above, intensity and pulse duration criteria may also be used to filter out the pulses unrepresentative of the gas velocity. The filtering of the undesirable signals is, for example, carried out in a time-moving window of duration $\Delta t2$.

During a third phase 503, the frequency signals accepted as output of the second phase 502 are used in combination over a time period $\Delta t3$ shorter or of the same duration as $\Delta t$, the time period $\Delta t3$ being much longer than $\Delta t2$, for example approximately 100 times longer than the time period $\Delta t2$. The time period $\Delta t3$ is nevertheless sufficiently short that the velocity of the flow of gas observed is quasi-invariant over this time period $\Delta t3$. For example, the frequencies of these accepted frequencies are averaged over this time period $\Delta t3$ to obtain a consolidated result free of noise. This result is a single Doppler frequency, which corresponds to the observed velocity of the flow of gas. Because, during the second phase, undesirable signals corresponding to inconsistent velocities were rejected, the precision of the frequency estimated during this combination third phase 503 is improved.

FIG. 6a shows a first exemplary implementation of the first phase 501 of the method according to the invention. During a first step 601, the digital signal 460 undergoes frequency filtering so as to detect the pulses backscattered by particles of size at least equal to that expected. This first step 601 notably allows an estimation of the frequency of a received pulse to be sought and to eliminate small possibly noise-like pulses. The frequency of a pulse is contained in the band of interest $[F_{min}, F_{max}]$ corresponding to the interval between the minimum expected velocity and the maximum expected velocity.

According to one way of implementing the method according to the invention, a bank of band-pass filters of adaptable widths is employed to perform a spectral division of the digital signal 460. In other words, the frequency band of interest is divided into several sub-bands, each of these sub-bands being associated with a band-pass filter 611, 612, 613. Advantageously, the sum of the pass bands of the filters 611, 612, 613 covers the whole frequency band of interest $[F_{min}, F_{max}]$. Furthermore, the width of the filters 611, 612, 613 is preferably chosen as a function of the expected pulse duration. In other words, the longer the expected pulse duration the smaller the divisions. However, the sub-bands may be chosen so as to partially overlap one another, notably to increase the reliability with which pulses having a frequency that lies between two adjacent filters are detected.

According to another way of implementing the method according to the invention, FFTs (fast Fourier transforms) are applied to portions of the digital signal 460. This method has the advantage of requiring fewer hardware resources than the use of polyphase filters such as those presented in FIG. 6a because this method requires fewer computations. Nevertheless, in contrast to the detection by polyphase filters which entails processing discrete in frequency but continuous in time, the use of FFT has the drawback of needing to chop the digital signal 460 in time. Thus, FFTs are preferably applied within a moving window, to maximise the probability of pulse detection. A level of window overlap equal to 50%, for example, is a good compromise between cost and performance. Advantageously, since the frequency of a pulse is inversely proportional to its duration, the analysis of the frequency signal output by the FFT may be performed by smaller and smaller sub-zones as higher frequencies are approached.

At the end of this first step 601, if a pulse is present in the digital signal, one or more consecutive filters 611, 612—depending on the width of the sub-bands chosen—produce as output a signal 611*a*, 612*a*, 613*a*. These filters 611, 612 transmit their output signals 611*a*, 612*a*, 613*a* to a module 630 for determining the frequency of the detected pulse. Several pulses with different frequency may be detected.

For example, during a second step 603, an amplitude threshold is applied by the module 630 for determining the frequency of the pulse to the signals detected in the frequency sub-bands corresponding to these filters 611, 612. If the amplitude of these signals is below the threshold, these signals are not considered as indicating a pulse and are therefore filtered out. When this is not the case, the maximum-amplitude frequency of the detected signal, is sought. In the case where several consecutive filters 611, 612 detect a signal, an interpolation (linear or otherwise) may permit the determination of the maximum-amplitude frequency, notably when the spectrum of the expected signal is of Gaussian waveform.

According to one embodiment, the module 630 for determining the frequency of the pulse detected uses a probabilistic decision operator which estimates, for each frequency in the band of interest, the probability that a detected pulse is of this frequency as a function of the power output 611*a*, 612*a*, 613*a* from each filter 611, 612, 613. The most probable frequencies are selected, as a function of the chosen criterion or criteria, in the example as a function of the power output 611*a*, 612*a*, 613*a* from the filters and the power values already observed in the past. A maximum likelihood algorithm may, for example, be employed. At the output of the module 630, no frequency, one frequency or several frequencies are indicated, depending on, respectively, whether the digital signal 460 is carrying no pulse during the time period Δt1 analysed, whether the digital signal is carrying a single pulse or whether the signal is carrying several pulses of different frequencies.

FIG. 6*b* shows, a second exemplary implementation of the first phase 501 of the method according to the invention. Compared with the first method according to the invention, an additional step 602 of correlating the digital signal 460 with the expected waveform of the signal is added after the first step 601.

When the pulse is produced by the backscatter from a particle small compared to the wavelength (or indeed a substantially spherical particle), the waveform of the beam emitted by the focusing optics 401 being known, it follows that the waveform of the pulse backscattered by such a particle centred in the waist 101 and of given velocity is also known beforehand. Knowing, at the end of the first step 601, the frequency sub-band in which a pulse is detected (and therefore the speed of the particle), each of the filter outputs may be correlated with a reference signal of the expected waveform and of a duration inversely proportional to the principal frequency (for example, the central frequency) of the filter associated with said sub-band. When neither the phase nor the instant of arrival of the pulse of the digital signal 460 are known, the correlation may be carried out with respect to the energy or the amplitude of the signal and by sliding the reference signal at each count of a digital clock.

The frequencies obtained by the first phase 501 of the method and stored in memory over the time period Δt2 may be transformed into image data representing the pulses on a time-frequency graph, as illustrated in FIG. 7. Each frequency obtained during an interval Δt1 at the end of the first phase 501 is represented on this image by a dot the colour of which depends on the amplitude of the frequency detected. When a pulse is due to the backscatter of the light beam by a large particle passing through the illuminated field non-centrically, this pulse has the appearance of a sloping line in the image so formed, because the pulse is linearly frequency-modulated.

To detect these undesirable pulses, known in-image shape recognition algorithms may be used. In the case in point, such an algorithm is parameterized to detect an oblique segment in the time-frequency image of the stored pulses. For example, certain algorithms, such as the Hough transform, are used in the automotive field to efficiently detect white lines in road images with a view to realizing self-driving vehicles. International patent application WO 2006/042810, which describes an algorithm for passively sorting moving targets detected by radar, may also be consulted.

When however this type of algorithm requires hardware and/or software resources that are too onerous to be applied to systems operating in real time, simpler algorithms may be implemented. For example, it is possible to seek a velocity model from one end of an image segment. More precisely, once a frequency F1 is detected during an interval Δt1 of first phase 501, an automaton is activated. This automaton next looks for, among the frequencies found in the following intervals Δt1, frequencies which when grouped with the frequency F1 form an oblique segment. The automaton must then take into account the fact that certain particles, and more particularly large particles, are not always perfectly spherical, since, when a particle has an irregular shape, the signal that it backscatters may take the form of an intermittent signal 702 (FIG. 7) made up of several short-duration pulses. It is therefore not satisfactory for the automaton to observe only consecutive intervals Δt1.

In the case of onboard aircraft anemometry, the signal possibly backscattered by the ground may be filtered out by identifying frequencies having the same values continuously over the time period Δt2. In a time-frequency image of these pulses, the trace due to the ground has the aspect of a continuous horizontal line, the signal backscattered by the ground not being frequency-modulated.

All the frequencies considered as being part of an undesirable signal are marked and/or deleted. Thus, the third phase 503 of the method does not take into account said frequencies when estimating the Doppler frequency corresponding to the velocity of the flow of gas.

The anemometry method according to the invention allows the airspeed to be measured, from an aircraft, with a precision of less than 0.5 m/s.

FIG. 8 shows a second exemplary implementation of the first phase 501 of the method according to the invention, an anemometry being performed with several light beams pointed into the gas of which the velocity is desired to be measured. The method according to the invention is applied to each of said beams. In the example, the processing steps applied to each beam are those presented above in FIG. 6*b*. Advantageously, the filters 611, 612, 613 used in the execution of the first phase 501 of the method for a given beam are parameterized as a function of the measurements performed by the other beams. For example, in the case of an anemometry along three non-coplanar measurement axes the direction of which with respect to the flow of gas, is known, the Doppler frequencies estimated for the two first axes may be used to estimate, for the third axis, the probable duration of the pulses produced by backscatter from particles of expected size.

According to the embodiment shown in FIG. 8, the modules 630 for determining the frequency of the detected pulse are grouped into a single module 830 supplied with the measurements 501a, 501b, 501c, 501a', 501b', 501c', 501a'', 501b'', 501c'' from the various axes. This module 830 may thus analyse the overall consistency of the various detected frequencies so as to reject undesirable pulses more reliably. The optical axes may converge on the same measurement volume; in this case, the particle will not produce the same frequency shift signature for each of the axes. On the contrary, if the axes do not converge, it is impossible to detect the same particle at the same instant.

When several particles simultaneously pass through the light beam, several options are possible. According to a first option corresponding to a situation in which many particles are detected in a time, the "abnormal" pulse due to multiple simultaneous particles may be immediately rejected, knowing that sufficient "normal" pulses exist. According to a second option corresponding to a situation in which a small number of particles are detected, although exceptionally several particles have passed through the beam simultaneously, several hypotheses are established: the presence of one particle, of two particles, of three particles etc. Next, the digital signal 460 is divided into a sum of several particles, according to each of these hypotheses. If the signal-to-noise ratio so allows, the most probable hypothesis is next determined so as finally to consider several independent pulses.

The invention claimed is:

1. A single-particle anemometry method comprising the continuous emission of a light beam through a gas containing particles, said light beam being focused onto a measurement volume, and a step of detecting a signal backscattered by particles passing through said measurement volume, said backscattered signal comprising a pulse for each particle passage across the field of the light beam, the method comprising at least the following phases:
   determining in a time period Δt the frequency of each of the pulses within the backscattered signal;
   distinguishing the pulses based on duration and/or intensity and/or frequency-modulation criteria; and
   estimating displacement velocity of said light beam relative to the gas from several of the frequencies determined over the time period Δt excluding those corresponding to the pulses distinguished during the distinguishing step.

2. The single-particle anemometry method according to claim 1, wherein the phase of determining the pulse frequency or frequencies included in the backscattered signal further comprises a step of filtering said backscattered signal with a bank of band-pass filters, frequency bands of said band-pass filters together covering a frequency band comprising Doppler frequencies corresponding to all possible gas displacement velocities.

3. The single-particle anemometry method according to claim 2, wherein a spectral width of the band-pass filters is chosen depending on an expected duration of the pulses within the backscattered signal.

4. The single-particle anemometry method according to claim 2, the method further comprising: at an output of at least one of the bank of band-pass filters, a step of correlating the backscattered signal produced by said output with a reference signal, the duration of which is inversely proportional to a principal frequency of said band-pass filter and a waveform of which is that of the emitted light signal.

5. The single-particle anemometry method according to claim 2, wherein each output signal from the bank of band-pass filters is assigned a pulse-presence probability value, said pulse-presence probability value being a function of the power of the signal at an output of at least one of the bank of band-pass filters.

6. The single-particle anemometry method according to claim 1, wherein a Fourier transform is applied to the backscattered signal, said Fourier transform being applied to a time-moving window, each frequency spectrum produced by an application of said Fourier transform being divided into frequency sub-zones for detecting a pulse in one of said frequency sub-zones, a width of said frequency sub-zones increasing as the frequency decreases.

7. The single-particle anemometry method according to claim 1, wherein the pulse distinction phase detects linearly frequency-modulated pulses by generating a time-frequency image of the frequencies associated with the pulses detected in the backscattered signal as a function of time, then executing a shape recognition algorithm to identify in the said time-frequency image oblique segments corresponding to the linearly frequency-modulated pulses.

8. The single-particle anemometry method according to claim 1, wherein the frequencies corresponding to the pulses within the backscattered signal, the duration of which is greater than a threshold value, are filtered out during a pulse distinction phase so as to be excluded during a gas displacement velocity estimation phase.

9. The single-particle anemometry method according to claim 1, wherein the frequencies corresponding to the pulses within the backscattered signal, the intensity of which is greater than a threshold value, are filtered out during a pulse distinction phase so as to be excluded during a gas displacement velocity estimation phase.

10. The single-particle anemometry method according to claim 9, wherein the gas displacement velocity estimation is carried out by determining a Doppler frequency shift $F_D$ equal to an average of the frequencies considered during said as displacement velocity estimation, and then by calculating a Doppler velocity corresponding to the Doppler frequency shift $F_D$.

11. The single-particle anemometry method according to claim 1, comprising a light source and a series of units for detecting the signals backscattered by the particles illuminated by said light beam, and a signal processing module implementing the method of single-particle anemometry.

12. The single-particle anemometry method according to claim 11, carried by an aircraft in order to measure its airspeed, wherein the emitted light beam is directed at an angle of illumination of between 30° and 70° to a velocity vector of the aircraft.

13. The single-particle anemometry method according to claim 12, wherein the light beam is focused close to the fuselage of the aircraft, at a distance of between 10 cm and several meters therefrom.

* * * * *

UNITED STATES PATENT AND TRADEMARK OFFICE
CERTIFICATE OF CORRECTION

PATENT NO. : 8,325,328 B2
APPLICATION NO. : 12/842872
DATED : December 4, 2012
INVENTOR(S) : Alain Renard et al.

It is certified that error appears in the above-identified patent and that said Letters Patent is hereby corrected as shown below:

Column 12, claim 10, line 45, please replace "to an average of the frequencies considered during said as" with --to an average of the frequencies considered during said gas--.

Signed and Sealed this
Nineteenth Day of February, 2013

Teresa Stanek Rea
*Acting Director of the United States Patent and Trademark Office*